US012336965B2

United States Patent
Messner-Rugova et al.

(10) Patent No.: US 12,336,965 B2
(45) Date of Patent: Jun. 24, 2025

(54) STOPPER DEVICE, MEDICAMENT CONTAINER, AND METHOD FOR MIXING TWO SUBSTANCES IN A MEDICAMENT CONTAINER

(71) Applicant: Vetter Pharma-Fertigung GmbH & Co. KG, Ravensburg (DE)

(72) Inventors: Fatbardha Messner-Rugova, Meckenbeuren (DE); Markus Eggensberger, Bad Schussenried (DE)

(73) Assignee: Vetter Pharma-Fertigung GmbH & Co. KG, Ravensburg (DE)

( * ) Notice: Subject to any disclaimer, the term of this patent is extended or adjusted under 35 U.S.C. 154(b) by 452 days.

(21) Appl. No.: 17/255,977

(22) PCT Filed: Jun. 28, 2019

(86) PCT No.: PCT/EP2019/067479
§ 371 (c)(1),
(2) Date: Dec. 23, 2020

(87) PCT Pub. No.: WO2020/007752
PCT Pub. Date: Jan. 9, 2020

(65) Prior Publication Data
US 2021/0113433 A1    Apr. 22, 2021

(30) Foreign Application Priority Data

Jul. 3, 2018   (DE) .......................... 102018210941.9

(51) Int. Cl.
*A61J 1/20*    (2006.01)
*A61M 5/24*    (2006.01)
(Continued)

(52) U.S. Cl.
CPC ........... *A61J 1/2041* (2015.05); *A61J 1/2089* (2013.01); *A61J 1/2093* (2013.01); *A61J 1/2096* (2013.01);
(Continued)

(58) Field of Classification Search
CPC ...... A61J 1/2041; A61J 1/2089; A61J 1/2093; A61J 1/2096; A61J 1/062; A61M 5/2448;
(Continued)

(56) References Cited

U.S. PATENT DOCUMENTS 2,688,966 A * 9/1954 Huber ................. A61M 5/2448
                                                      604/90
3,326,215 A * 6/1967 Sarnoff ................. A61M 5/284
                                                      604/90
(Continued)

FOREIGN PATENT DOCUMENTS

DE    3635574 A1 * 10/1986
EP    2399564 A1 * 12/2011    ............ A61J 1/2093
(Continued)

OTHER PUBLICATIONS

International Preliminary Report on Patentability for PCT/EP2019/067479 dated Jan. 14, 2021, 9 pages.
(Continued)

*Primary Examiner* — Rebecca E Eisenberg
*Assistant Examiner* — Ted Yang
(74) *Attorney, Agent, or Firm* — Sheppard Mullin Richter & Hampton LLP (57) ABSTRACT

A stopper device (1) seals off a medicament container (45) with a stopper element (3), wherein the stopper device is designed to seal the medicament container (45) in an axial direction of a center axis (M) of the medicament container (45), wherein the stopper device (1) is at least partially insertable into the medicament container (45), and the
(Continued)

stopper element (3), in the intended installation position in the medicament container (45), is displaceable along the center axis (M) of the medicament container (45). The stopper device (1) has a retention region (23) with at least one retention means (5), wherein a closure element (7), in a first functional state of the stopper device (1), is retained by the retention means (5) in a fixed position relative to the stopper element (3), in particular retained releasably in a retention position on the stopper element (3), in such a way that a cavity (29) is formed between the closure element (7) and the stopper element (3).

15 Claims, 2 Drawing Sheets (51) Int. Cl.
*A61M 5/28* (2006.01)
*A61M 5/315* (2006.01)

(52) U.S. Cl.
CPC .......... *A61M 5/2448* (2013.01); *A61M 5/284* (2013.01); *A61M 2005/2462* (2013.01); *A61M 2005/287* (2013.01); *A61M 5/31596* (2013.01); *A61M 2005/31598* (2013.01)

(58) Field of Classification Search
CPC .......... A61M 5/284; A61M 2005/2462; A61M 2005/287; A61M 2005/31598; A61M 5/31596
See application file for complete search history.

(56) References Cited

U.S. PATENT DOCUMENTS

| | | | | |
|---|---|---|---|---|
| 3,789,670 A | * | 2/1974 | Rosenwald | G01N 1/2042 366/241 |
| 3,986,645 A | * | 10/1976 | Baldwin | A61M 5/31511 222/386 |
| 4,116,240 A | * | 9/1978 | Guiney | A61M 5/31596 604/92 |
| 4,153,057 A | * | 5/1979 | Kobel | A61J 1/2096 604/90 |
| 4,254,768 A | * | 3/1981 | Ty | A61M 5/284 604/518 |
| 5,114,411 A | * | 5/1992 | Haber | A61J 1/2089 604/203 |
| 5,125,892 A | * | 6/1992 | Drudik | A61M 5/31596 604/200 |
| 5,158,546 A | * | 10/1992 | Haber | A61J 1/2093 604/416 |
| 5,330,048 A | * | 7/1994 | Haber | A61J 1/2093 604/203 |
| 5,335,773 A | * | 8/1994 | Haber | B65D 25/08 604/203 |
| 5,352,196 A | * | 10/1994 | Haber | A61J 1/2089 604/416 |
| 5,360,410 A | * | 11/1994 | Wacks | A61M 5/322 604/206 |
| 5,419,445 A | * | 5/1995 | Kaesemeyer | A61J 11/04 215/11.4 |
| 5,593,028 A | * | 1/1997 | Haber | B65D 25/085 604/203 |
| 5,725,500 A | * | 3/1998 | Micheler | B01F 31/24 604/82 |
| 9,943,648 B2 | * | 4/2018 | Glocker | A61M 5/286 |
| 10,124,122 B2 | * | 11/2018 | Zenker | A61M 5/348 |
| 2001/0004681 A1 | * | 6/2001 | Landau | A61M 5/30 604/70 |
| 2003/0111552 A1 | * | 6/2003 | Vedrine | A61M 5/284 239/533.1 |
| 2003/0136799 A1 | | 7/2003 | Peuker et al. | |
| 2003/0163084 A1 | * | 8/2003 | Griffiths | B01F 35/32021 604/82 |
| 2007/0060875 A1 | * | 3/2007 | Bassarab | A61M 5/2448 604/84 |
| 2011/0073501 A1 | * | 3/2011 | Wu | B65D 81/32 206/219 |
| 2011/0166596 A1 | * | 7/2011 | Delmotte | A61J 1/2096 606/214 |
| 2011/0196292 A1 | * | 8/2011 | Matusch | A61M 5/1782 604/82 |
| 2012/0109098 A1 | | 5/2012 | Sargeant et al. | |
| 2012/0155214 A1 | * | 6/2012 | Faccioli | A61B 17/8822 366/130 |
| 2014/0102918 A1 | * | 4/2014 | Eitrheim | A61J 1/2093 206/219 |
| 2016/0265022 A1 | * | 9/2016 | Yang-Woytowitz | C12M 23/38 |
| 2016/0296703 A1 | * | 10/2016 | Bailey | A61M 5/285 |
| 2018/0200443 A1 | * | 7/2018 | Keadle | A61M 5/19 |
| 2020/0054524 A1 | | 2/2020 | Messner-Rugova | |

FOREIGN PATENT DOCUMENTS

| | | | | |
|---|---|---|---|---|
| FR | 2930140 A1 | * | 10/2009 | .......... A61J 1/2093 |
| JP | H0553767 U | | 7/1993 | |
| JP | H0722980 U | | 4/1995 | |
| RU | 2058132 C1 | | 4/1996 | |
| WO | 2001062175 | | 8/2001 | |
| WO | WO-0162175 A1 | * | 8/2001 | .............. A61C 5/62 |
| WO | WO-0162176 A1 | * | 8/2001 | .............. A61C 5/66 |
| WO | WO-03053494 A2 | * | 7/2003 | ............ A61M 5/007 |
| WO | WO-2012139995 A1 | * | 10/2012 | .......... A61L 2/0088 |
| WO | WO-2015199336 A1 | * | 12/2015 | ............. A61B 17/56 |

OTHER PUBLICATIONS

International Search Report and Written Opinion for PCT/EP2019/067479 dated Oct. 16, 2019, with English translation of ISR, 12 pages.

* cited by examiner

Fig. 1

STOPPER DEVICE, MEDICAMENT CONTAINER, AND METHOD FOR MIXING TWO SUBSTANCES IN A MEDICAMENT CONTAINER

CROSS-REFERENCE TO RELATED APPLICATIONS

This application is a U.S. National Stage Application under 35 U.S.C. § 371 of International Application No. PCT/EP2019/067479, filed Jun. 28, 2019, which claims priority to DE 10 2018 210 941.9, filed Jul. 3, 2018, the contents of which are incorporated to the present disclosure by reference.

The invention relates to a stopper device, a medicament container having such a stopper device, and a method for mixing two substances that are stored separately from one another in terms of flow in such a medicament container.

Stopper devices, medicament containers, and methods of the type discussed here are known. Two substances stored separately from one another in terms of flow are typically mixed with one another in a medicament container embodied as a two-chamber system. A first substance of the two substances is arranged in a first, proximal chamber and a second substance is arranged in a second, distal chamber.

In such a medicament container, the first, proximal chamber is delimited in the proximal direction by a first stopper device, in particular an end stopper, in the distal direction by a second stopper device, especially a center stopper, and in the radial direction by an inner wall of the medicament container. The second, distal chamber is delimited in the proximal direction by the second stopper device, in the radial direction by the inner wall of the medicament container, and in the distal direction by the medicament container tip, which is preferably closed by a closure cap.

Before the medicament container is initialized, the proximal chamber is closed in a fluidically tight manner with respect to the distal chamber and the surroundings of the medicament container. The second stopper device is not shifted into a mixing position until initialization, which establishes a fluidic connection between the two chambers via a bypass, so that the two substances can mix with one another, provided the second stopper device is arranged in the mixing position. In particular, by exerting an in particular manual pressure on the first stopper device, the contents of the proximal chamber, that is, the first substance, are pressed out of the proximal chamber and transported into the distal chamber via the bypass, the volume of the proximal chamber being reduced and the second stopper device remaining in the mixing position until the first stopper device butts against the second stopper device.

The initialization thus includes application of pressure to the first stopper device in the distal direction, causing displacement of the first stopper device. Due to the displacement and the fluidic sealing off of the proximal chamber, pressure is also applied to the second stopper device, so that the latter is also displaced in the distal direction until it reaches the mixing position. In the mixing position, the bypass causes the pressure to equalize, so that the second stopper device is no longer subjected to the pressure on one side. In such conventional medicament containers, for initialization and thus for mixing the two substances, it is therefore necessary for both stopper devices to be displaced.

Before the initialization, that is, before the use of the known method for mixing the substances, the two substances are stored separately from one another, as a result of which the safety and/or shelf-life of the substances is increased. The initialization is only carried out before a planned application, in particular an injection, the stopper devices in the medicament container being displaced along a center axis of the medicament container into an axial position in which mixing is possible, in particular via a bypass.

In order to increase the sliding ability of the stopper devices in the medicament container and thus to achieve a safe medicament container which assures aseptic storage and/or application of a medical agent, the inner wall of the medicament container is siliconized. As a result, however, it is not possible, or at least not safe, to place in such known medicament containers substances which react on contact with the siliconized inner wall, in particular in an unintentional manner. Temporally and/or spatially separated filling of the respective chambers is complicated, since the medicament container must be rotated and/or closed after filling the first chamber and/or the filling of the second chamber must be completed before the first chamber can be filled. In addition, mixing the two substances in such a medicament container is not optimal, particularly because of the typically small dimensions of the bypass.

In addition, with such conventional stopper devices it is not possible, or it is only possible under difficult conditions, to design an ampule or injection bottle, also called a vial, as a multi-chamber system, in particular a double-chamber system, since these vessels are embodied open only at one end. Thus, when axially sealing stopper devices are displaced in such vessels, pressure fluctuations occur which make displacement in the axial direction more difficult and ultimately limit such displacement. In particular, the second stopper device functioning as a center stopper cannot easily be displaced far enough into such a vessel. In addition, in such vessels displacement of the second stopper device into the mixing position is not possible, or at least is significantly more difficult and therefore not practicable, because of the pressure fluctuations that result.

The object of the invention is to create a stopper device, a medicament container, and a method for mixing two substances in a medicament container, wherein the aforesaid disadvantages are avoided. In particular, it is the object of the invention to create a medicament container and a stopper device in which unstable substances, in particular powder medicines which must not come into contact with a siliconized inner wall, can be safely stored and mixed with a second substance.

The object is achieved by creating the subject matter of the independent claims. Advantageous configurations result from the subordinate claims.

The object is achieved in particular by creating a stopper device for sealing off a medicament container, the stopper device having a stopper element, wherein the stopper device is designed to seal off the medicament container in an axial direction of a center axis of the medicament container, in particular by means of the stopper element, wherein the stopper device is at least partially insertable into the medicament container and in the intended installation position in the medicament container the stopper element is displaceable along the center axis of the medicament container, and wherein the stopper device, in particular the stopper element, has a retention region with at least one retention means. The stopper device is distinguished in that, in a first functional state of the stopper device, a closure element is retained by means of the retention means in a fixed position relative to the stopper element, in particular retained releasably directly on the stopper element, in such a way that a cavity is formed between the closure element and the stopper element. In this way, a substance provided in particular for mixing can be arranged in this cavity of the stopper device and stored sealed off with respect to the surroundings without a medicament container being necessary for this purpose. A medicament container can be filled with two substances in a simple manner in two separate steps that are largely independent of one another. It is also possible to safely store an unstable substance, in particular powder medicines, in such a stopper device, since contact with silicone, in particular a siliconized inner wall of a medicament container, is prevented. By means of such a stopper device, it is also possible and made simple to form a double-chamber system in an injection vial and/or ampule, since no center stopper is required for separating two chambers.

A substance is understood here in particular to be a medicinal substance, very particularly a medicinal active substance and/or adjuvant.

The stopper device, in particular the closure element and the stopper element, is/are embodied to receive such a substance, in particular a medicinal agent, in the cavity, preferably aseptically, the cavity preferably being fluidically tight. The stopper device preferably has a plastic or comprises plastic.

A stopper element is understood here to be a stopper, in particular an end stopper, for a medicament container. The stopper element preferably has an elastic material or comprises such a material. The stopper element particularly preferably comprises an elastomer and/or soft plastic. In a sealing region, the stopper element is preferably at least partially elastic and/or along a circumferential surface in the sealing region which, when in the intended installation position in a medicament container, faces an inner wall of the medicament container and/or an insertion sleeve and is positioned tightly against this, for sealing contact with the inner wall and/or the insertion sleeve. The medicament container is thus sealed in the axial direction, in particular by the tight contact of the stopper element and/or stopper device against an inner wall of the medicament container, so that at least one chamber of the medicament container designed for receiving a substance is delimited in the axial, preferably proximal direction.

A medicament container is understood here to be in particular a syringe, carpule, ampule and/or injection bottle, a so-called vial. Such medicament containers, in particular syringes and carpules, are embodied as a single-chamber system or multi-chamber system, in particular a dual-chamber system.

The stopper device and/or the stopper element are preferably at least partially insertable, particularly preferably completely insertable, into the medicament container. In the inserted state, that is, in the intended installation position in the medicament container, the stopper element can preferably be displaced along the center axis by means of a piston rod and/or a dispensing device.

The retention means in the retention region is preferably embodied integral with the stopper element. The retention means preferably has a region that is elastic in the radial direction, so that in the first functional state the closure element is retained by means of radial retaining forces. The retention means and the stopper element particularly preferably comprise an elastic material, in particular rubber and/or soft plastic.

In the first functional state, the closure element is preferably retained in the retention position such that it is not possible to displace the stopper element without simultaneously displacing the closure element. There is thus preferably a mechanical contact between the stopper element and the closure element, at least in the first functional state of the stopper device.

According to a further development of the invention, it is provided that in the first functional state the cavity is fluidically sealed off with respect to a wall, in particular the inner wall, of the medicament container. Contact with a siliconized surface is thus prevented and the safety for a substance stored in the cavity is high.

In the first functional state, the cavity is preferably delimited exclusively by the closure element and the stopper element and is embodied thereby. It is provided in particular that the cavity is embodied by a hollowing in the stopper element and/or in the closure element, the cavity being closable by means of the closure element, in particular being closed in the first functional state. The closure element thus seals off the cavity, so that a substance stored therein is fluidically sealed off with respect to surroundings, in particular with respect to the medicament container. In particular, a fluidic seal with respect to an inner wall of a medicament container is created given the installation position in the medicament container is as intended. Thus, a tight cavity for safe storage of a substance is created even without a medicament container.

According to a further development of the invention, it is provided that in a second functional state the cavity is open, wherein the closure element is not retained in the retention position by the retention means. It is thus possible to open the cavity and therefore to cause a first substance stored therein to mix with a second substance stored in a chamber of a medicament container. When the stopper device is in the intended installation position in the medicament container, in the second functional state the cavity is thus open in particular with respect to the chamber of the medicament container, wherein there is a fluidic connection between the cavity and the chamber in which the second substance is preferably stored. Mixing of two substances, in particular the first substance and the second substance, can thus be carried out simply and safely in a medicament container with such a stopper device.

Alternatively, however, it is also possible that in the second functional state the closure element is not completely released by the retention means, but instead continues to be retained at least partially on the stopper element, in particular in the retention region, wherein the closure element however no longer seals off the cavity, so that there is a fluidic connection to the outside of the cavity, in particular into the chamber of the medicament container.

As an alternative or in addition, it is provided that even when the stopper device is not inserted in the medicament container, in the first functional state the closure element is retained in a fixed position with respect to the stopper element. Thus, the stopper device can be used flexibly and a medicament container for safe storage of the first substance in the stopper device is not required.

The stopper element of the stopper device is particularly preferably embodied as an end stopper for a medicament container, wherein it is provided that the stopper device and, at least in the first functional state, the stopper element are arranged at the end, in particular at the proximal end, of a chamber of a medicament container. An end stopper arranged at the end in a medicament container is understood here to mean in particular a stopper that seals off the medicament container, wherein all of the in particular medicinal substances included in the medicament container and/or all of the chambers designed for them are arranged proceeding from the stopper in the distal direction. On the other hand, proceeding from the end stopper arranged at the end in the proximal direction, no chambers or regions are provided which are designed for safely storing a substance, in particular a medicinal substance. Thus, such an end stopper separates an aseptic region provided distal to the end stopper from a region provided proximal to the end stopper, which region is only subject to lower cleanliness requirements, in particular no cleanliness requirements.

According to a further development of the invention, it is provided that the closure element is embodied as a mixing body, in particular as a ball, for the medicament container and/or, in the second functional state, is arranged in the medicament container so that it can move freely, in particular independently of the stopper element. In the second functional state, the in particular spherical closure element is preferably arranged loose in the medicament container. This improves the mixing of the first substance with the second substance by shaking the medicament container, the mixing body causing additional turbulence in the medicament container.

According to a further development of the invention, it is provided that, in the first functional state, the stopper element has a discharge projection on its side facing the closure element and the discharge projection is at least partially oriented in the direction of the closure element. The discharge projection can be embodied elastic at least in a longitudinal direction along a center axis when in the intended installation position in a medicament container, but it is so stable that the closure element can be displaced by the discharge projection out of the retention position, in which the cavity is tightly closed, in an axial direction, in particular in the distal direction of the medicament container, wherein the retention forces applied by the retention means are overcome. An axial resistance force, that is, the strength of the discharge projection, which counteracts an axial deformation of the discharge projection, is therefore greater than the retention force applied by the retention means.

An axial force required to move the closure element out of the retention position, in particular in the distal direction, is preferably applied to the piston rod by a piston rod and manual pressure. The discharge projection preferably projects in the distal direction. Thus, even after positioning in the medicament container, the closure element can be moved out of the retention position in a simple manner and the stopper device can thus be transitioned to the second functional state. The cavity and the substance arranged therein, and, when in the intended installation position in a medicament container, the chamber of the medicament container and the second substance stored therein are fluidically sealed off, in particular in a sterile manner, with respect to the surroundings of the medicament container, which is in particular closed with a cap.

When arranged as intended in the rotationally symmetrical, in particular at least substantially cylindrical medicament container, the discharge projection is preferably arranged concentric with a longitudinal axis of the medicament container. Thus, the forces to be applied in the distal direction are minimal and the seal between the stopper device and an inner wall of the medicament container is particularly high due to the symmetry formed thereby.

An outer wall of the stopper element in the retention region is preferably offset radially inward compared to an outer wall in the sealing region, so that, when in the intended installation position in a medicament container, circumferential free space is formed between the stopper element and the inner wall of the medicament container to allow the retention means to divert. Due to the free space, it is easy to remove the closure element from the retention region, since the material of the stopper element in the retention region does not have to be compressed as strongly, but instead only has to be deformed into the free space.

According to a further development of the invention it is provided that, at least in an ejection state of the stopper device, but preferably also in the first functional state, a side and/or tip and/or end face of the discharge projection facing the closure element is positioned against the closure element. The ejection state thus denotes the state of the stopper device in which the closure element is still in the first functional state, but would transition immediately to the second functional state through a minimal force on the stopper device in the distal direction and a pressure exerted thereby from the discharge projection onto the closure element. The ejection state is thus the limit state between the first functional state and the second functional state. The forces to be applied in the distal direction are thus minimal and the closure element is moved out of the retention region in a particularly controlled manner.

According to a further development of the invention, it is provided that the closure element has at least one first locking means, wherein the retention means of the stopper device has at least one second locking means embodied to correspond to the first locking means and arranged in the retention region on a side of the stopper element facing the closure element, wherein, in the first functional state, the first locking means and the second locking means engage in one another in a locking manner. The closure element is thus securely held on the stopper element.

The closure element preferably has at least one locking receptacle, in particular a ring-like circumferential locking groove, wherein the retention means of the stopper device has at least one locking projection embodied corresponding to the locking receptacle, which is arranged in the retention region on a side of the stopper element facing the closure element, wherein, in the first functional state, the locking projection engages in the locking receptacle. In this case, therefore, the first locking means is embodied as a locking receptacle and the second locking means as a locking projection. When the stopper device is in the intended installation position in the medicament container, the locking receptacle is preferably embodied in the circumferential direction about a center axis of the medicament container. The closure element is thus held in the retention position in a particularly reliable manner.

Alternatively, however, it is also possible for the first locking means to be embodied as a locking projection and the second locking means as a locking receptacle, so that the retention means has the locking receptacle and the closure element has the locking projection. In this case, as well, the closure element is securely held in the retention position.

According to a further development of the invention, it is provided that the stopper device has an insertion sleeve enveloping the stopper element, in particular in the circumferential direction, wherein an outer side of a sleeve wall is preferably embodied for tight contact against an inner wall of the medicament container. The stopper element here is positioned tightly against an inner side of the sleeve wall opposing the outer side. The insertion sleeve is preferably embodied rotationally symmetrical, in particular cylindrical, at least in sections. The sleeve wall has a finite, specific thickness in the radial direction, so that a receding region that widens in the radial direction is formed in the distal direction at the distal end of the insertion sleeve when the stopper device is in the intended installation position in the medicament container. The retention region of the stopper device is preferably prestressed radially inward when inserted in the insertion sleeve in that the retention region is radially compressed by the insertion sleeve. After the retention region has been displaced into this receding region, the retention region is not prestressed as strongly and is preferably relaxed. The retention region thus widens outward in the radial direction, and the closure element is no longer retained. In particular, in this displacement position of the stopper element or retention region, the locking projection is released from the locking receptacle so that the positive fit connection between the closure element and the stopper element thus formed is eliminated. This creates a particularly simple-to-operate release mechanism for the closure element, with the aid of which two substances can be mixed in a cylinder-symmetrical medicament container without a bypass, wherein only the stopper element must be displaced in the distal direction.

The insertion sleeve of the stopper device is preferably wedge-shaped at its distal end, in particular in the receding region, and in particular has a drainage slope for the stopper element that runs around the circumference, so that the radial widening in the receding region occurs uniformly and gradually. The production of the stopper device is thus simplified, the closure element being displaced into a first functional position assigned to the first functional state. This also therefore improves safety, in particular the sealing of the cavity and/or the chamber of the medicament container, as well as handling during mixing and/or dispensing of the mixed substances.

According to a further development of the invention it is provided that the insertion sleeve is designed as a finger rest and has at least one radially protruding finger plate at a proximal end, which finger plate is embodied to be gripped from behind by a finger. The finger plate is preferably embodied to run completely around a center axis or divided into at least two individual, opposing plates. It is important that the finger plate protrudes radially in particular with respect to an outer wall of a medicament container in which the stopper device can be arranged, so that it can be grasped from behind and thus the handling of the medicament container is simplified.

According to a further development of the invention it is provided that the insertion sleeve has a fastening structure for fastening the insertion sleeve to a medicament container, wherein the fastening structure preferably has a receptacle for the medicament container, in which receptacle the proximal end of the medicament container, in particular a proximal, radial thickening of the medicament container, can be received in a locking and/or clamping manner. The fastening structure is preferably formed by an axially extending recess that runs around the center axis and is open in the distal direction, and into which the proximal end of the medicament container can be inserted, wherein it is finally brought to the locking and/or clamping receptacle. The stopper device can thus be easily and quickly attached to a medicament container.

When in the intended installation position in a medicament container, the stopper element, in particular the retention means, is preferably arranged in the retention region at a distance from an inner wall of the medicament container and/or from an inner side of the insertion sleeve. It is thus possible for the retention means in the retention region to be pushed apart radially, in particular when a force is exerted on the stopper element, and for the closure element to be released thereby.

The object is also achieved in particular by creating a medicament container with a preferably cylindrical base body which comprises in particular glass, and with a stopper device according to one of the preceding claims, wherein the stopper device is arranged moved into the medicament container such that the stopper element a seals off a proximal end of the medicament container with respect to an in particular tightly closable chamber of the base body, wherein the chamber is delimited in the radial direction by an inner wall of the base body and in the distal direction by a closable outlet opening of the base body and/or a closure cap. The chamber is also preferably embodied rotationally symmetrical, essentially cylindrical. When viewed from the stopper device, the chamber is provided in a distal direction of the medicament container and is designed to receive a medicinal substance, in particular a medical active ingredient and/or adjuvant, especially a solvent for a powder medicine.

A closed, in particular sterile, volume for receiving the second substance is thus particularly preferably embodied by the chamber. In the second functional state of the stopper device, the closure element of the stopper device is arranged in particular loose in this chamber. The closure element is preferably larger than the outlet opening of the base body so that the closure element cannot be moved out of the chamber through the outlet opening. The closure element is thus embodied as a mixing body.

According to a further development of the invention, it is provided that the outlet opening of the base body, at least on its side facing the chamber, has a geometry, in particular a cruciform cross section, which differs from a side facing the outlet opening, in particular from each side of the closure element, such that a fluidically tight closure of the outlet opening is prevented by the closure element. The closure element is preferably embodied round, in particular spherical. This prevents the outlet opening from being blocked by the closure element in the second functional state. In particular, the closure element is unsuitable for fluidically sealing the outlet opening, so that the closure element cannot prevent the first and/or second substance from being discharged from the medicament container, particularly in the second functional state.

A radial extension of the non-circular geometry is preferably greater than a radial extension of a side of the closure element that is suitable for positioning against the outlet opening. Alternatively or additionally, the closure element has a curvature on its outer surface which differs from a curvature of a bottom wall of the medicament container that has the outlet opening.

If the closure element has locking receptacles, the closure element, with the exception of these locking receptacles, is round, in particular spherical. In particular, it is provided that the ring-shaped locking groove is arranged on the equator of the spherically embodied closure element, wherein an upper hemisphere portion of the closure element is separated from a lower hemisphere portion of the closure element by the locking groove.

The closure cap is preferably arranged distally on the base body for closing the outlet opening. A closure cap is understood here to mean an element that closes the chamber, in particular also a closed injection device.

A first substance is arranged in the cavity of the stopper device, a second substance being arranged in the chamber of the medicament container, these two substances being intended for mixing and the point in time of mixing being selectable by a user, since the two substances are arranged in volumes fluidically sealed off from one another, specifically the chamber of the medicament container and the cavity of the stopper device, wherein the seal between the chamber and the cavity can be broken by the user using pressure on the stopper device.

The medicament container preferably has a finger rest which is suitable for applying a suitable force to a dispensing device, in particular a piston rod, when the active substances are dispensed from the medicament container. The finger rest is embodied integral with the base body or, if the stopper device is arranged in an insertion sleeve having the finger plate, is embodied separately from the base body. In both cases, however, the finger rest is retained securely on the base body, so that usage, in particular the dispensing of a substance, in particular both substances, from the medicament container takes place in the same way in both exemplary embodiments.

According to a further development of the invention, it is provided that a dispensing device, in particular a piston rod, is provided, wherein a convex, in particular spherical, conical, and/or tapering projection is provided at the distal end of the dispensing device. The distal end is understood here to be the end of the dispensing device facing the stopper device, this end acting directly on the in particular proximal end of the stopper device when the substances are dispensed from the medicament container. The projection is preferably centered relative to the center axis of the medicament container, so that the dispensing device, when acting on the stopper device, applies a maximum force to center region thereof.

According to a further development of the invention, it is provided that the stopper element is embodied elastic, wherein it is deformable by means of the projection of the dispensing device, in particular using manual exertion of pressure on the dispensing device in the distal direction, wherein the discharge projection of the stopper element has greater strength in the axial direction than the pressure required to move the closure element. The strength of the stopper element in the axial direction is realized due to its structural design and/or the material. In particular, the discharge projection here is conical. The closure element can thus be easily moved out from the retention region.

Strength is understood here to mean in particular mechanical resistance which prevents elastic and/or plastic material failure. The strength can preferably be quantified as mechanical stress, in particular as pressure, or as force, and can preferably be converted into a pressure. In this case, the strength in the axial direction is preferably greater than the pressure required to move the closure element. The strength of the discharge projection thus prevents in particular elastic and/or plastic deformation of the discharge projection.

The object is also achieved in particular in that a method is created for mixing two substances stored separately from one another in terms of flow in a medicament container, in particular according to one of the previously described exemplary embodiments with a stopper device in particular according to one of the previously described exemplary embodiments, wherein a first substance of the two substances is arranged in the cavity of the stopper device and a second substance of the two substances is arranged in the chamber of the base body, wherein the stopper device is acted upon with a force in the distal direction, wherein the fluidic separation of the two substances from one other is broken, wherein the stopper device, in particular the stopper element, in the retention region, is deformed, at least partially, due to the distal application of force, in particular radially, such that the closure element is moved out of the retention position. It is particularly advantageous that the application of the force and the resulting deformation and/or displacement are sufficient to break the fluidic seal between the first and the second substance, so that the two substances can be mixed safely and easily with simple means. In addition, the advantages already mentioned above result with regard to the exemplary embodiments of the medicament container and the stopper device.

In particular, a method is created for mixing two substances stored separately from one another in terms of flow in a medicament container, in particular according to one of the previously described exemplary embodiments with a stopper device in particular according to one of the previously described exemplary embodiments, wherein a first substance of the two substances is arranged in the cavity of the stopper device and a second substance of the two substances is arranged in the chamber of the main body, wherein the stopper device is subjected to a pressure, in particular finger pressure, in the distal direction, wherein the fluidic separation of the two substances from one another is eliminated, wherein the stopper device, in particular the stopper element in the retention region, through the distal application of pressure, is at least partially deformed, in particular radially, such that the closure element is displaced from the retention position. It is particularly advantageous that displacement of the stopper device and/or stopper element is not necessary for opening the cavity and thus for mixing the substances and in particular is not provided. An application of pressure and the resulting deformation are sufficient to break the fluidic seal between the first and the second substance. Thus, mixing in a medicament container, in particular a syringe or carpule, with a closed outlet opening, but also in an injection vial or an ampule with such a stopper device, can be carried out easily, avoiding large pressure fluctuations in the containers.

The stopper element is thus preferably deformed at its proximal end, in particular by the action of the projection of the dispensing device, on the stopper device. Due to the elastic embodiment and the conical, in particular tapered, embodiment of the projection, the retention region of the stopper element is widened radially such that the closure element retained by the retention means is released.

So that the retention region can be widened sufficiently radially, when the stopper device is in the intended installation position in the medicament container, it is preferably provided that the stopper device in the retention region is not positioned directly against an inner wall of the medicament container. Instead, a free space is provided in the retention region, between the inner wall of the medicament container and an outer wall of the stopper element, into which free space the stopper element, in particular the retention means, is forced in order to release the closure element.

As already explained in connection with the medicament container, the closure element closes the cavity in the retention position, the cavity being sealed off in particular with respect to the chamber of the medicament container.

In particular, a method is created for mixing two substances stored separately from one another in terms of flow in a medicament container, in particular according to one of the exemplary embodiments described above, with a stopper device in particular according to one of the exemplary embodiments described above, wherein a first substance of the two substances is arranged in the cavity of the stopper device and a second substance of the two substances is arranged in the chamber of the base body, wherein the stopper device is displaced in the distal direction, wherein the fluidic separation of the two substances is eliminated, wherein the retention region relaxes radially during the distal displacement of the stopper device, wherein the retention of the closure element in the retention position is released. The retention region of the stopper device, in particular of the stopper element, is here preferably under a radial prestress in that the retention region is compressed relative to a relaxed position. In a relaxed region, in particular the receding region at the distal end of the insertion sleeve, which has a widened inner radius compared to the insertion sleeve, the retention region relaxes after the stopper element has been moved therein. The closure element can thus be moved out of the retention region in a simple manner, and the cavity can be opened thereby. Relaxing is understood here to mean in particular a widening deformation of the prestressed stopper device, in particular of the stopper element in the retention region.

It is particularly preferably provided that, in a method according to one of the previously described embodiments, the medicament container is shaken after the cavity has been opened, that is, after the stopper device has been transitioned to the second functional state. This improves the mixing of the two substances.

According to a further development of the invention, it is provided that in a method according to one of the embodiments described above the stopper device in the medicament container is displaced into a distal end position in order to fully dispense the first and/or second substance, in particular a medicament, wherein in the end position the closure element is preferably completely received in the cavity, and/or the cavity is completely filled by the closure element. A distal end position is understood here to mean in particular a position of the stopper element at the distal end of the chamber of the base body, wherein the stopper element is positioned in particular against the outlet opening. The dead volume is thus minimal when using a medicament container of the type described here, in particular when carrying out the methods described here.

The descriptions of the method, the stopper device, and the medicament container are to be understood as complementary to one another. In particular, features of the stopper device and/or of the medicament container that have been explicitly or implicitly described in connection with the method are preferably individual features of the stopper device and/or of the medicament container or features combined with one another. The stopper device and/or the medicament container are preferably embodied to carry out at least one of the method steps described in connection with the method. Method steps that have been explicitly or implicitly described in connection with the stopper device and the medicament container are preferably individual steps of a preferred embodiment of the method or steps in combination with one another. In particular, within the scope of the method, at least one step is preferably provided that results from at least one feature of the stopper device and/or of the medicament container.

Overall, it can be seen that with the stopper device, the medicament container, and the method described here, the mixing of two substances in a medicament container is improved. Handling is also improved, in particular during a manufacturing process, since the filling of the cavity with the first substance can take place independently of the filling of the medicament container with the second substance. In particular, the cavity of the stopper device is also already fluidically sealed off without a medicament container, so that a substance stored therein is already safely stored even without a medicament container, and, in addition, when the stopper device is in the intended installation position in the medicament container, cannot come into contact with a siliconized inner wall of the medicament container. Thus, in particular aseptic powder filling in a two-chamber system is possible by means of the stopper device described here, the medicament container described here, and the method described here, even in the previously siliconized medicament container, wherein the safety and chemical stability of the filled powder is assured. Furthermore, the shelf life of the substances is increased with the stopper device, medicament container, and methods described here.

The invention is explained in greater detail below with reference to the drawing.

Figure 1:
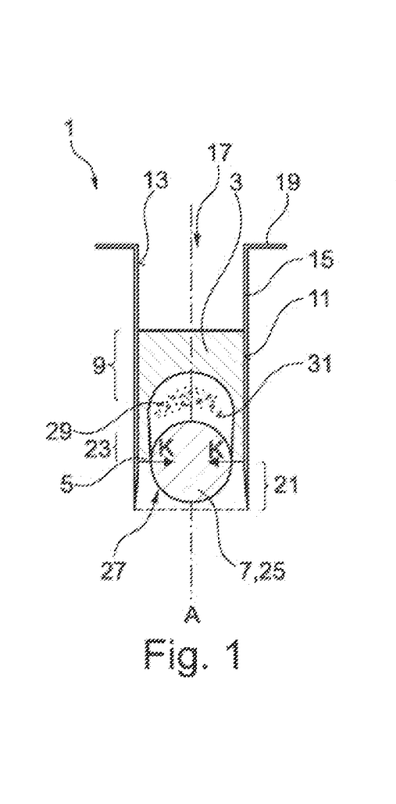
FIG. 1 is a longitudinal section of a stopper device according to a first exemplary embodiment.

FIG. 1 shows a stopper device 1 in a longitudinal sectional view with a stopper element 3, a retention means 5, and a closure element 7. The stopper element 3 has a sealing region 9 in which a circumferential surface 11 of the stopper element 3 is embodied in a sealing manner. In the sealing region 9, the stopper element 3 is positioned in particular tight against an inner side 13 of an insertion sleeve 15, so that after the stopper device 1 has been installed in a medicament container (not shown here), the medicament container is sealed in an axial direction. The stopper device 1 shown here is embodied rotationally symmetrical to a rotational axis A. In an intended installation position in a medicament container, the rotational axis coincides with a center axis of the medicament container. The insertion sleeve 15 thus envelops the stopper element 3 in the circumferential direction about the rotational axis A and is positioned tight against the stopper element 3 in the radial direction.

At its upper, proximal end in FIG. 1, the insertion sleeve 15 has a finger plate 19 running around a proximal opening 17. Using this finger plate 19, the stopper device 1 and/or a medicament container can be retained, in particular in order to apply a force to the stopper element 3 in the distal direction. At its lower, distal end in FIG. 1, the insertion sleeve 15 has a receding region 21, wherein the ends of the insertion sleeve 15 in the receding region 21 are embodied wedge-shaped, in particular as a drainage slope, in the longitudinal section through the stopper device 1 shown here.

The retention means 5 is provided here in a retention region 23 of the stopper device 1, wherein the retention region 23 is embodied by a lower axial segment of the stopper element 3 in FIG. 1. In this retention region 23, the stopper element 3, which is embodied elastic, is compressed in relation to a relaxed position, so that the retention means 5 is radially prestressed.

The stopper element 3 is arranged displaceable along the rotational axis in the insertion sleeve 15, that is, displaceable upwards and/or downwards in FIG. 1. After the stopper device 1 has been inserted into the medicament container (not shown here), the stopper element 3 can be displaced, in particular downwards, in a distal direction, wherein the medicament container is sealed off axially in each distal displacement position by means of the stopper device 1, in particular the stopper element 3 and the insertion sleeve 15.

The stopper device 1 is shown in FIG. 1 in a first functional state, wherein the closure element 7 is releasably retained, in a fixed position relative to the stopper element 3, in a retention position by means of the retention means 5. In the exemplary embodiment shown here, the closure element 7 is held in particular by a positive fit, wherein the retention means 5 acts on the closure element 7 with a force K radially inwards from all sides in the retention region 23, in particular due to the rotationally symmetrical embodiment. The closure element 7, which is embodied here in particular as a ball 25, is thus clamped in a lower, distal opening 27 of the stopper element 3.

The lower, distal opening 27 of the stopper element 3 is closed in a fluid-tight manner by the closure element 7. As a result, formed between the closure element 7 and the stopper element 3 is a cavity 29 in which a first substance 31, here in particular a powder medicine, is arranged. Thus, a fluidically tight cavity 29 is created here, in which the first substance 31 can be safely stored, a medicament container not being necessary in order to realize the fluidic seal.

As can be seen in FIG. 1, the closure element 7 does not project beyond a lower, distal end of the insertion sleeve 15, so that the closure element 7 is protected from unwanted displacement, in particular in the direction of the cavity 29, or any other disruptive displacement that might jeopardize the sealed nature of the cavity 29. The first substance 31 can thus be safely stored in this stopper device 1 and can be installed in a medicament container at any later point in time.

Figure 2:
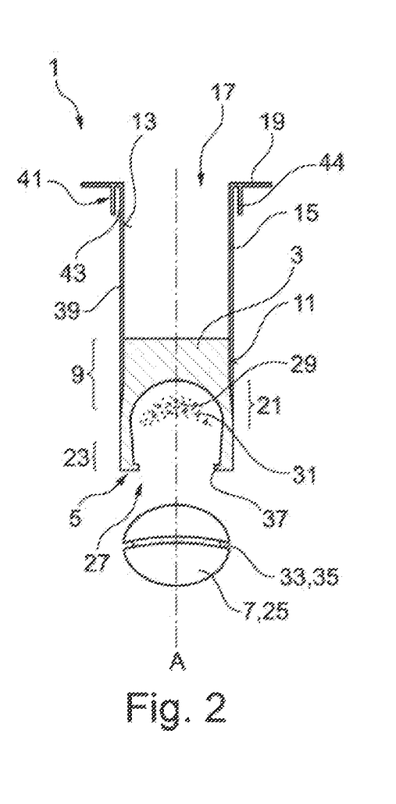
FIG. 2 is a longitudinal section of a stopper device according to a second exemplary embodiment.

FIG. 2 shows a stopper device 1 in a lateral sectional illustration according to a second exemplary embodiment. The stopper device 1 is shown here in particular in a second functional state, wherein the closure element 7 is not retained in the retention position by the retention means 5. Identical and functionally identical parts are provided with the same reference numbers, so that in this respect reference is made to the preceding description of the figure.

In contrast to the first exemplary embodiment shown in FIG. 1, the cavity 29 is open here in FIG. 2. The closure element 7 is not retained in the retention position by the retention means 5. The first substance 31 arranged in the cavity 29 can thus escape from the cavity 29.

As in FIG. 1, as well, the stopper element 3 here has the sealing region 9 and the retention region 23. In FIG. 2 it is also provided that the retention region 23 is prestressed radially inward, at least in the first functional state (not shown here), by being compressed, so that the closure element 7 is clamped in the lower, distal opening 27 of the stopper element 3. Moving the stopper element 3 into the second functional state shown here causes a part of the stopper element 3, in particular the retention region 23, to be moved out of the insertion sleeve 15, so that the stopper element 3 in the retention region 23 and thus also the retention means 5 can relax radially outward. Due to the radial relaxing, the retention forces K on the closure element 7 decrease and the closure element 7 is no longer retained in the retention position.

In addition to the retention mechanism described above, which is also realized in the same way in the first exemplary embodiment, shown in FIG. 1, a locking receptacle 33 is provided on the closure element 7 in FIG. 2. This locking receptacle 33 is formed here in particular by a locking groove 35 running around the equator of the former. Corresponding to this locking groove 35, it is provided that the retention means 5 has a locking projection 37 which runs around the lower, distal opening 27 and which, in the first functional state, engages in the locking groove 35 in a positive fit. An additional safeguard for retaining the closure element 7 in the retention position is thus created.

To release the closure element 7 from the retention position, in the second exemplary embodiment for the stopper device 1 shown in FIG. 2, in the first functional state it is necessary for the retention region 23 to be compressed at least the length of the locking projection 37. The length of the locking projection is understood here to mean in particular the extension of the locking projection in the radial direction. This ensures that the restoring force resulting from the prestress radially expands the retention means 5, in particular the locking projection 37, at least far enough that the locking projection 37 is no longer engaging the locking groove 35. Furthermore, it is preferably provided that a thickness of a wall 39 of the insertion sleeve 15 is just as thick as or is thicker than the length of the locking projection 37. When in the intended installation position in a medicament container with a cylindrical interior space, this ensures that the retention region 23 can relax far enough to release the positive fit between the locking groove 35 and the locking projection 37.

It can also be seen in FIG. 2 that the insertion sleeve 15 has a fastening structure 41 for fastening the insertion sleeve 15 to a medicament container. This fastening structure 41 has a receptacle 43 for a medicament container, in which the proximal end of the medicament container can be received in a locking and/or clamping manner. The stopper device 1 can thus be fastened to, in particular clipped on, the medicament container in a simple manner. Alternatively or in addition, the stopper device 1 can preferably be bonded, in particular welded on, welded to, and/or glued to the medicament container by means of the fastening structure 41, so that it is in particular reliably assured that the interior of the medicament container is sterile.

The receptacle 43 shown in FIG. 2 extends in the direction of the center axis over only a small segment of the insertion sleeve 15. However, in an alternative exemplary embodiment (not shown here), the receptacle 43 preferably extends over an entire axial extent of the insertion sleeve 15. In the alternative exemplary embodiment (not shown here), this is preferably realized in that an outer wall 44 of the receptacle 43 extends in particular parallel to the inner side 13 of the insertion sleeve 15 over the entire axial extent of the insertion sleeve 15. In the first functional state, the outer wall 44 of the receptacle 43 particularly preferably extends over an entire axial extent of the closure element 7, preferably beyond it, in the distal direction. In this way, an in particular additional seal between the outer wall 44 of the receptacle 43 and an outer wall of the medicament container can be effected, so that the sterility and the safety of the medicament container are increased.

Figure 3:
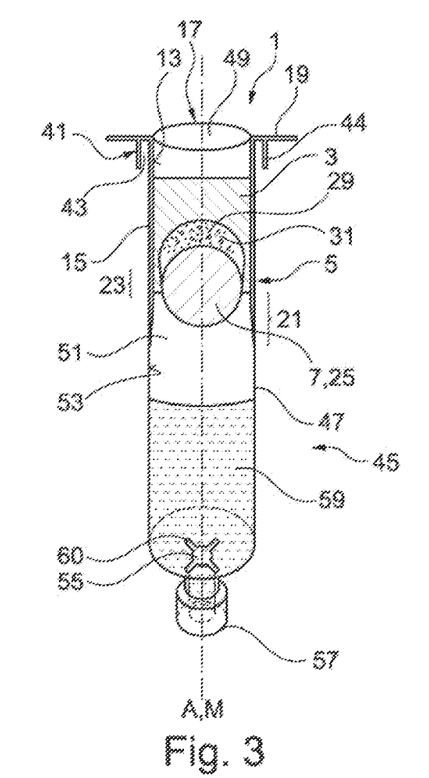
FIG. 3 is a longitudinal section of a medicament container according to a first exemplary embodiment with a stopper device according to the second exemplary embodiment.

FIG. 3 shows a medicament container 45 with a stopper device 1 according to the exemplary embodiment described in FIG. 2. The medicament container 45 has a cylindrical base body 47 and a proximal end 49. A chamber 51 of the medicament container 45, which is designed to receive a medicinal substance, is delimited by an in particular siliconized inner wall 53 of the base body 47, the stopper device 1, and, in the distal direction, by a distal outlet opening 55. The distal outlet opening 55 is closed here in FIG. 3 by means of a closure cap 57. A second substance 59, in particular a solvent for the powder medicine, is arranged in the chamber 51.

As the stopper device 1 is in the intended installation position in the medicament container 45, the rotational axis A of the stopper device 1 coincides with a center axis M of the medicament container 45, wherein the stopper element 3 is displaceable along the center axis A, in particular in the distal direction.

For the sake of clarity, the locking structures shown in FIG. 2, namely the locking groove 35 and the locking projection 37, are not shown here in FIG. 3, but are nevertheless provided. The retention forces K are also provided here, but are not shown for the sake of clarity.

The stopper device 1 is in the first functional state here, so that the cavity 29 is tightly closed. The first substance 31 arranged in the cavity 29 is therefore fluidically sealed from the chamber 51, the second substance 59 arranged therein, and also the in particular siliconized inner wall 53 of the medicament container 45. A reaction between the silicone and the first substance 31 is thus prevented.

On its side facing the chamber 51, the outlet opening 55 of the base body 47 has a geometry which differs from the shape of the closure element 7. In particular, this geometry is realized here by a non-circular cross-section 60, so that the closure element 7, which is spherical with the exception of the locking groove 35, cannot be sealingly positioned against the outlet opening 55 and the outlet opening 55 thus always remains unclosed from the inside on its side facing the chamber 51. The cross-section 60 is preferably at least partially cruciform in shape.

Figure 4:
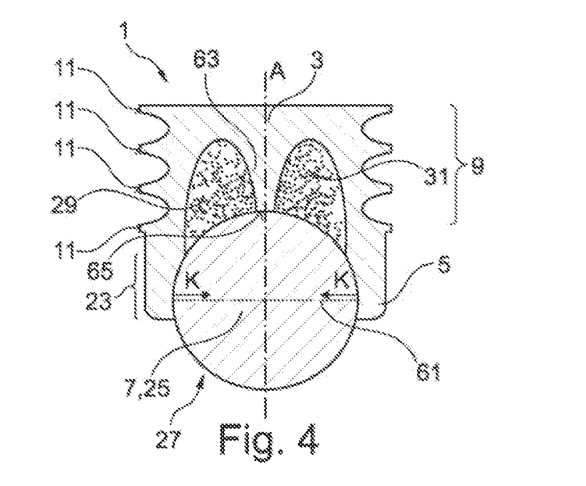
FIG. 4 is a longitudinal section of a stopper device according to a third exemplary embodiment.

FIG. 4 shows a stopper device 1 in a lateral sectional view according to a third exemplary embodiment. Identical and functionally identical parts are provided with the same reference numbers, so that reference is made to the preceding description of the figures.

In contrast to the first and second exemplary embodiments of the stopper device 1, the stopper device 1 shown here does not have an insertion sleeve 19.

Like the previously described exemplary embodiments of the stopper device 1, the third exemplary embodiment of the stopper device 1, which is shown in FIG. 4, has a stopper element 3 which is embodied to seal off a medicament container 45 in an axial direction. The stopper device 1 shown here can in particular be completely inserted into a medicament container 45, wherein the stopper element 3, here in particular the complete stopper device 1, is embodied displaceable along the center axis 11 in the medicament container 45.

The stopper device 1 has a retention region 23 with a retention means 5 and a sealing region 9, which has a plurality of circumferential surfaces 11 of the stopper element 3. Each of the plurality of circumferential surfaces 11 is preferably embodied be positioned against an inner wall 53 of the medicament container 45 in a sealing manner when the stopper device 1 is in the intended installation position in the medicament container 45.

The retention means 5 retains a closure element 7 in a retention position. The closure element 7, which is designed as a ball 25, is retained directly against the stopper element 3.

A cavity 29 is formed between the closure element 7 and the stopper element 3 and in FIG. 4 appears to be divided into two parts due to the lateral sectional view, but is a contiguous, annular cavity 29 due to the rotational symmetry about the rotational axis A.

The retention means 5 retains the closure element 7 in the retention position, in particular in a non-positive fit, in that holding forces K, proceeding from the retention region 23 of the stopper element 3, act radially inward and thereby clamp the closure element 7 in a lower, distal opening 27. In addition, the tight contact of the stopper element 3 with the closure element 7 and thus the sealing of the cavity 29 is therefore ensured in the retention region 23.

In addition to this clamping effect of the retention means 5, in the exemplary embodiment of the stopper device 1 shown in FIG. 4, in the first functional state shown here the retention region 23 of the stopper element 3 extends at least partially beyond an equator 61 of the ball 25 in the distal direction, wherein the retention region 23 is positioned against the closure element 7 so that the closure element 7 is gripped from behind by the retention means 5 in the distal direction. The closure element is thus also held in a positive fit.

An equator 61 is understood here in particular to be a closed circumferential line about the closure element 7 which includes a surface that is perpendicular to the rotational axis A and has a radius that corresponds to a radius of the closure element 7, wherein the radius is at least locally, preferably globally, maximal with respect to the longitudinal extension center axis.

In contrast to the two previously described exemplary embodiments in FIGS. 1, 2, and 3, on its side facing the closure element 7 the stopper element 3 has a discharge projection 63 which is at least partially oriented in the direction of the closure element 7. This discharge projection 63 protrudes from the stopper element 3 in a cone-like manner, in particular in the shape of a truncated cone, and a front end face 65 of the discharge projection 63, which is at its bottom in FIG. 4, butts against the closure element 7.

Thus, the stopper device 1 is in an ejection state here in which even a slight deformation, in particular an axial action of the discharge projection 63 on the closure element 7, can cause the closure element 7 to be moved out of the retention position.

Figure 5:
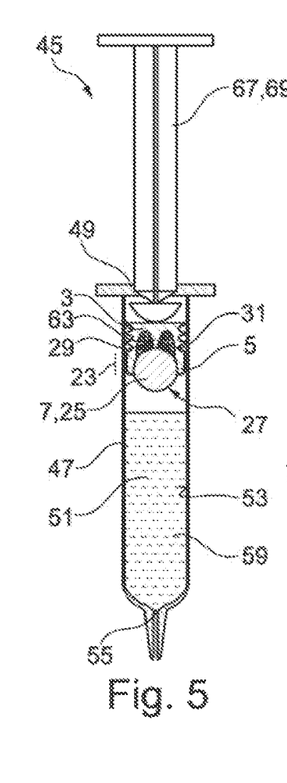
FIG. 5 is a longitudinal section of a medicament container according to a second exemplary embodiment with a stopper device according to the third exemplary embodiment in a first functional state.
Figure 6:
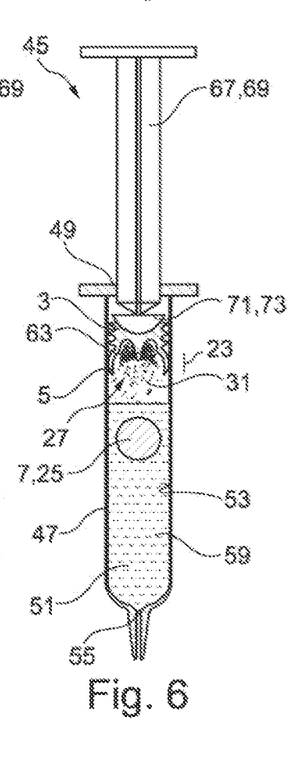
FIG. 6 is a longitudinal section of a medicament container according to the second exemplary embodiment with a stopper device according to the third exemplary embodiment in a second functional state; and, FIG. 7 is a longitudinal section of a medicament container according to the second exemplary embodiment with a stopper device according to the third exemplary embodiment in an end position of the stopper device in the medicament container.
Figure 7:
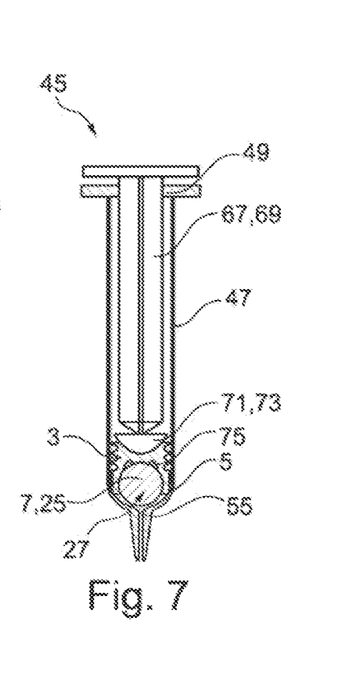

FIGS. 5 to 7 show a medicament container 45 with a stopper device 1 according to the embodiment described in FIG. 4, wherein the stopper device 1, in various functional states, is arranged in the intended installation position in the medicament container. A method for mixing two substances stored from one another in terms of flow, namely a first substance 31 and a second substance 59, in the medicament container 45 is explained below using these figures.

In FIG. 5, the first substance 31 is enclosed in the cavity 29 of the stopper device in a fluidically tight manner by the stopper element 3 and the closure element 7. The stopper device 1 shown in FIG. 5 is therefore in the first functional state.

In order to release the closure element 7 from the retention position and thus open the cavity 29, the stopper element 3 is subjected to a pressure in the distal direction, as shown in FIG. 6. Due to the resulting deformation, in particular in the proximal region of the stopper element 3, a distal end and thus also the lower, distal opening 27 of the stopper element 3 is spread radially outward, so that, on the one hand, the frictional connection caused by the retention means 5 and, on the other hand, the positive fit caused by the gripping from behind via the equator 61 of the closure element 7 are eliminated. As a result, the closure element 7 is no longer retained in the retention position and is moved out of the retention position due to gravity and/or a shaking movement. The cavity 29 is thus now open, and the first substance 31 mixes with the second substance 59 due to the fluidic opening of the cavity 29. The closure element 7 is designed here in particular as a mixing body which, when the medicament container 45 is shaken, leads to additional turbulence in the chamber 51 of the medicament container 45, accelerating and/or improving mixing.

It should be emphasized here that a displacement of the stopper element 3 is not absolutely necessary in order to open the cavity 29. Instead, just the application of the pressure in the distal direction is sufficient to bring about a suitable deformation of the stopper element 3.

The deformation of the stopper element 3 is caused here in particular by means of a dispensing device 67, which is embodied as a piston rod 69. A convex, spherical segment-shaped projection 73 is provided at a distal end 71 of the dispensing device 67. This projection 73 is embodied rotationally symmetrical with a center axis M of the medicament container 45. The projection 73 is at its maximum centrally on the center axis M. Thus, when the stopper element 3 is acted upon with pressure by means of the dispensing device 67, the deformation is greatest in a center region in the immediate vicinity of the center axis M, so that the retention means 5 in the retention region 23 is spread lever-like in at least two preferably opposing, radial directions, particularly preferably on all sides in each radial direction.

FIG. 7 shows the medicament container 45 in an end position, the closure element 7 being almost completely received in the cavity 29, so that the cavity 29 itself is almost completely filled by the closure element 7. A residual amount of the first substance and/or of the second substance in the chamber 51 of the medicament container 45 is thus minimal. To this end, the stopper element 3, in particular the discharge projection 63, is embodied elastic so that the discharge projection 63 is deformed in the end position, so that a residual volume 75 of the cavity 29 is minimal. Nevertheless, as shown in FIGS. 5 and 6, the discharge projection 63 has sufficient strength to move the closure element 7 out of the retention position against the retention forces K, wherein the retention forces K are preferably reduced by a deformation of the stopper element 3.

Overall, it can be seen that by means of such a stopper device 1 and such a medicament container 45, a first, in particular unstable, substance 31 is pre-filled in the stopper device 1 in a safe and reaction-free manner and tightly in terms of flow, and, in particular by means of such a method a second substance 59 in the medicament container 45 can be added for mixing, wherein the risk of a reaction, in particular an unwanted reaction with a siliconized inner wall 53 of the medicament container 45, is minimal. In addition, handling is improved compared to conventional stopper devices 1 and/or medicament containers 45, since the stopper device 1 can be pre-filled with the first substance 31 independently of the medicament container 45 and, if necessary, packaged without a medicament container 45 being necessary. In addition, the dead volume in such a medicament container 45, that is, a residual amount of the first substance 31 and/or of the second substance 59 in the chamber 51, is minimized.

The invention claimed is:

1. A stopper device (1) for sealing off a medicament container (45) with a stopper element (3),
   wherein the stopper device (1) is embodied to seal off the medicament container (45) in an axial direction of a center axis (M) of the medicament container (45),
   wherein the stopper device (1) is at least partially insertable into the medicament container (45) and in an intended installation position in the medicament container (45) the stopper element (3) is displaceable along the center axis (M) of the medicament container (45),
   wherein the stopper device (1) has a retention region (23) with at least one retention means (5),
   wherein, in a first functional state of the stopper device (1), a closure element (7) is releasably retained in a fixed position relative to the stopper element (3) by means of the retention means (5), in such a way that a cavity (29) is formed between the closure element (7) and the stopper element (3), and
   wherein the closure element (7) has at least one first locking means,
   wherein the retention means (23) of the stopper device (1) has at least one second locking means embodied corresponding to the first locking means and arranged in the retention region (23) on a side of the stopper element (3) facing the closure element (7), and
   wherein, in the first functional state, the first locking means and the second locking means engage in one another in a locking manner.

2. The stopper device (1) according to claim 1, characterized in that in a second functional state the cavity (29) is open, wherein the closure element (7) is not retained in a retention position by the retention means (5).

3. The stopper device (1) according to claim 1, characterized in that the closure element (7), in a second functional state, is arranged freely movable in the medicament container (45).

4. The stopper device (1) according to claim 1, characterized in that, in the first functional state, the stopper element (3) has a discharge projection (63) on a side of the discharge projection (63) facing the closure element (7) and the discharge projection (63) is at least partially oriented in a direction of the closure element (7).

5. The stopper device (1) according to claim 4, characterized in that, at least in an ejection state of the stopper device (1), the discharge projection (63), with a side and/or tip facing the closure element (7), is positioned against the closure element (7).

6. The stopper device (1) according to claim 1, characterized in that the stopper device (1) has an insertion sleeve (15) enveloping the stopper element (3), wherein an outer side of a sleeve wall is contacted against an inner wall (53) of the medicament container (45).

7. The stopper device (1) according to claim 6, characterized in that the insertion sleeve (15) is designed as a finger rest and has at least one radially protruding finger plate (19) at a proximal end, which finger plate (19) is grasped from behind by a finger.

8. The stopper device (1) according to claim 7, characterized in that the insertion sleeve (15) has a fastening structure (41) for fastening the insertion sleeve (15) to the medicament container (45), wherein the fastening structure (41) has a receptacle (43) for the medicament container (45), in which receptacle (43) the proximal end (49) of the medicament container (45) is received in a locking and/or clamping manner.

9. A medicament container, comprising a base body (47) and a stopper device (1) for sealing off the medicament container (45) with a stopper element (3),
   wherein the stopper device (1) is embodied to seal off the medicament container (45) in an axial direction of a center axis (M) of the medicament container (45), wherein the stopper device (1) is at least partially insertable into the medicament container (45) and in an intended installation position in the medicament container (45) the stopper element (3) is displaceable along the center axis (M) of the medicament container (45), wherein the stopper device (1) has a retention region (23) with at least one retention means (5), wherein, in a first functional state of the stopper device (1), a closure element (7) is releasably retained in a fixed position relative to the stopper element (3) by means of the retention means (5), in such a way that a cavity (29) is formed between the closure element (7) and the stopper element (3), wherein the stopper device (1) is arranged moved into the medicament container (45) such that the stopper element (3) seals off a proximal end (49) of the medicament container (45) with respect to a chamber (51) of the base body (47), wherein the chamber (51) is delimited in a radial direction by the inner wall (53) of the base body (47) and in a distal direction by an outlet opening (55) of the base body (47) and/or a closure cap (57), and wherein the stopper element (3) is elastic, wherein it is deformable by means of the projection (73) of the dispensing device (67), and wherein the discharge projection (63) of the stopper element (3) has a greater strength in the axial direction than the pressure required to move the closure element (7).

10. The medicament container according to claim 9, characterized in that the outlet opening (55) of the base body (47) has a geometry at least on a side of the outlet opening facing the chamber (51), which differs from a side of the closure element (7) facing the outlet opening such that a fluidically tight closure of the outlet opening (55) is prevented by the closure element (7).

11. The medicament container according to claim 9, characterized by a dispensing device (67), wherein a projection (73) is provided at a distal end (71) of the dispensing device (67).

12. A method for mixing two substances (31, 59) stored separately from one another in terms of flow in the medicament container (45) according to claim 9, wherein a first substance (31) of the two substances (31,59) is arranged in the cavity (29) of the stopper device (1) and a second substance (59) of the two substances (31,59) is arranged in the chamber (51) of the base body (47), wherein the stopper element (3) is acted upon with a force in the distal direction, wherein the fluidic separation of the two substances (31, 59) is eliminated, characterized in that the stopper device (1), is deformed, at least partially, due to the distal force application, such that the closure element (7) is moved out of a retention position.

13. A method for mixing two substances (31, 59) stored separately from one another in terms of flow in a medicament container (45), the medicament container (45) with a base body (47) and a stopper device (1) for sealing off a medicament container (45), with a stopper element (3), wherein the stopper device (1) is embodied to seal off the medicament container (45) in an axial direction of a center axis (M) of the medicament container (45), wherein the stopper device (1) is at least partially insertable into the medicament container (45) and in an intended installation position in the medicament container (45) the stopper element (3) is displaceable along the center axis (M) of the medicament container (45), wherein the stopper device (1) has a retention region (23) with at least one retention means (5), wherein, in a first functional state of the stopper device (1), a closure element (7) is releasably retained in a fixed position relative to the stopper element (3) by means of the retention means (5), in such a way that a cavity (29) is formed between the closure element (7) and the stopper element (3), wherein the stopper device (1) is arranged moved into the medicament container (45) such that the stopper element (3) seals off a proximal end (49) of the medicament container (45) with respect to a chamber (51) of the base body (47), wherein the chamber (51) is delimited in a radial direction by the inner wall (53) of the base body (47) and in a distal direction by an outlet opening (55) of the base body (47) and/or a closure cap (57), wherein a first substance (31) of the two substances (31,59) is arranged in the cavity (29) of the stopper device (1) and a second substance (59) of the two substances (31,59) is arranged in the chamber (51) of the base body (47), wherein the stopper element (3) is acted upon with a force in the distal direction, wherein the fluidic separation of the two substances (31, 59) is eliminated, characterized in that the stopper device (1), is deformed, at least partially, due to the distal force application, such that the closure element (7) is moved out of a retention position, wherein the stopper element (3) is displaced in the distal direction, wherein the fluidic separation of the two substances (31, 59) is eliminated, wherein the retention region (23) relaxes radially during a distal displacement of the stopper device (1), and wherein a retention of the closure element (7) in the retention position is released.

14. The method according to claim 13, characterized in that the medicament container (45) is shaken after the cavity (29) has been opened.

15. The method according to claim 13, characterized in that the stopper device (1) is displaced into an end position for a complete discharge of the two substances (31, 59) in the medicament container (45), wherein the closure element (7) is received in the end position in the cavity (29), and wherein the cavity (29) is completely filled by the closure element (7).

* * * * *